United States Patent
Sunwoo et al.

(10) Patent No.: US 9,138,509 B2
(45) Date of Patent: Sep. 22, 2015

(54) COMPOSITION FOR FILLING BONE DEFECTS

(75) Inventors: Moon Hae Sunwoo, Old Tappan, NJ (US); Victor A. Lizano, Jersey City, NJ (US); Arthur A. Gertzman, Flemington, NJ (US)

(73) Assignee: MUSCULOSKELETAL TRANSPLANT FOUNDATION, Edison, NJ (US)

( * ) Notice: Subject to any disclaimer, the term of this patent is extended or adjusted under 35 U.S.C. 154(b) by 1627 days.

(21) Appl. No.: 11/898,722

(22) Filed: Sep. 14, 2007

(65) Prior Publication Data

US 2009/0074871 A1 Mar. 19, 2009

(51) Int. Cl.
*A61K 9/14* (2006.01)
*A61L 27/44* (2006.01)
*A61L 27/36* (2006.01)
*A61L 27/38* (2006.01)
*A61L 27/46* (2006.01)
*A61L 27/54* (2006.01)
*A61L 27/58* (2006.01)

(52) U.S. Cl.
CPC .......... *A61L 27/446* (2013.01); *A61L 27/3608* (2013.01); *A61L 27/3804* (2013.01); *A61L 27/3847* (2013.01); *A61L 27/46* (2013.01); *A61L 27/54* (2013.01); *A61L 27/58* (2013.01); *A61L 2300/404* (2013.01); *A61L 2300/406* (2013.01); *A61L 2300/408* (2013.01); *A61L 2300/414* (2013.01); *A61L 2400/06* (2013.01); *A61L 2430/02* (2013.01)

(58) Field of Classification Search
CPC .......... A61L 27/46; A61L 27/12; A61L 27/58; A61L 27/425; A61L 27/227; A61L 27/0084; A61L 27/54; A61L 2300/414; A61K 33/42; A61K 31/74; A61K 33/06; A61K 38/00; A61K 38/39; C07K 14/475; C07K 16/00
See application file for complete search history.

(56) References Cited

U.S. PATENT DOCUMENTS

| | | | |
|---|---|---|---|
| 5,061,286 A | 10/1991 | Lyle | |
| 5,073,373 A | 12/1991 | O'Leary et al. | |
| 5,236,456 A | 8/1993 | O'Leary et al. | |
| 5,284,655 A | 2/1994 | Bogdansky et al. | |
| 5,290,558 A | 3/1994 | O'Leary et al. | |
| 5,298,254 A | 3/1994 | Prewett et al. | |
| 5,314,476 A | 5/1994 | Prewett et al. | |
| 5,356,629 A | 10/1994 | Sander et al. | |
| 5,405,390 A | 4/1995 | O'Leary et al. | |
| 5,439,684 A | 8/1995 | Prewett et al. | |
| 5,484,601 A | 1/1996 | O'Leary et al. | |
| 5,507,813 A | 4/1996 | Dowd et al. | |
| 5,510,396 A | 4/1996 | Prewett et al. | |
| 5,676,146 A | 10/1997 | Scarborough | |
| 5,702,677 A | 12/1997 | Shimp et al. | |
| 5,707,962 A | 1/1998 | Chen et al. | |
| 5,830,493 A | 11/1998 | Yokota et al. | |
| 5,895,426 A | 4/1999 | Scarborough et al. | |
| 5,899,939 A | 5/1999 | Boyce et al. | |
| 5,904,718 A | 5/1999 | Jefferies | |
| 5,968,556 A | 10/1999 | Atala et al. | |
| 5,980,948 A | 11/1999 | Goedemoed et al. | |
| 6,045,580 A | 4/2000 | Scarborough et al. | |
| 6,123,731 A | 9/2000 | Boyce et al. | |
| 6,162,258 A | 12/2000 | Scarborough et al. | |
| 6,180,605 B1 | 1/2001 | Chen et al. | |
| 6,180,606 B1 | 1/2001 | Chen et al. | |
| 6,293,970 B1 | 9/2001 | Wolfinbarger, Jr. et al. | |
| 6,294,041 B1 | 9/2001 | Boyce et al. | |
| 6,294,187 B1 | 9/2001 | Boyce et al. | |
| 6,309,659 B1 | 10/2001 | Clokie | |
| 6,311,690 B1 | 11/2001 | Jefferies | |
| 6,315,795 B1 | 11/2001 | Scarborough et al. | |
| 6,332,779 B1 | 12/2001 | Boyce et al. | |
| 6,340,477 B1 | 1/2002 | Anderson | |
| 6,425,949 B1 | 7/2002 | Lemaitre et al. | |
| 6,436,138 B1 | 8/2002 | Dowd et al. | |
| 6,440,444 B2 | 8/2002 | Boyce et al. | |
| 6,461,632 B1 | 10/2002 | Gogolewski | |
| 6,478,825 B1 | 11/2002 | Winterbottom et al. | |
| 6,565,884 B2 | 5/2003 | Nimni | |
| 6,569,200 B2 | 5/2003 | Wolfinbarger, Jr. et al. | |

(Continued)

FOREIGN PATENT DOCUMENTS

WO WO 02/28332 4/2002
WO WO 2004/011053 A1 2/2004

OTHER PUBLICATIONS

International Search Report for International Application No. PCT/US2008/010699, filed Sep. 12, 2008.
Written Opinion for International Application No. PCT/US2008/010699, filed Sep. 12, 2008.

*Primary Examiner* — Satyendra K Singh
(74) *Attorney, Agent, or Firm* — Greenberg Traurig, LLP

(57) ABSTRACT

The invention is directed toward an improved formable bone composition for application to a bone defect site to promote new bone growth at the site which comprises a new bone growth inducing compound of demineralized lyophilized allograft bone particles ranging from about 100 to 850 microns. The bone particles are mixed in an excipient carrier combination containing carboxymethylcellulose, sodium hyaluronate, and a sodium phosphate saline buffer, the carboxymethylcellulose component of the carrier ranging from about 5.0 to about 11.0% of the composition and the sodium hyaluronate component of the carrier ranging from about 0.3 to about 0.7% of the composition, the composition having a pH between 6.5-7.5.

16 Claims, No Drawings

(56) References Cited

U.S. PATENT DOCUMENTS

| | | |
|---|---|---|
| 6,599,520 B2 | 7/2003 | Scarborough et al. |
| 6,616,698 B2 | 9/2003 | Scarborough |
| 6,623,748 B2 | 9/2003 | Clokie |
| 6,630,153 B2 | 10/2003 | Long et al. |
| 6,685,626 B2 | 2/2004 | Wironen |
| 6,696,073 B2 | 2/2004 | Boyce et al. |
| 6,706,067 B2 | 3/2004 | Shimp et al. |
| RE38,522 E * | 5/2004 | Gertzman et al. ............ 424/423 |
| 6,752,831 B2 | 6/2004 | Sybert et al. |
| 6,776,800 B2 | 8/2004 | Boyer, II et al. |
| 6,808,585 B2 | 10/2004 | Boyce et al. |
| 6,843,807 B1 | 1/2005 | Boyce et al. |
| 6,846,853 B2 | 1/2005 | Shimp |
| 6,855,169 B2 | 2/2005 | Boyer, II et al. |
| 6,863,694 B1 | 3/2005 | Boyce et al. |
| 7,019,192 B2 | 3/2006 | Gertzman et al. |
| 7,045,141 B2 | 5/2006 | Merboth et al. |
| 7,063,726 B2 | 6/2006 | Crouch et al. |
| 7,153,518 B2 | 12/2006 | Wironen et al. |
| 7,163,691 B2 | 1/2007 | Knaack et al. |
| 7,179,299 B2 | 2/2007 | Edwards et al. |
| RE39,587 E * | 4/2007 | Gertzman et al. ............ 424/423 |
| 7,270,813 B2 | 9/2007 | Shimp et al. |
| 2002/0192263 A1 | 12/2002 | Merboth et al. |

\* cited by examiner

COMPOSITION FOR FILLING BONE DEFECTS

RELATED APPLICATIONS

There is no related application

FIELD OF INVENTION

The present invention is generally directed toward a surgical bone product and more specifically is an improved composition for filling bone defects using demineralized allograft bone particles, partially demineralized allograft bone particles mixed in a fluid carrier having an isotonic phosphate buffer and a high molecular weight viscous excipient.

BACKGROUND OF THE INVENTION

Surgical implants are designed to be biocompatible in order to successfully perform their intended function. Biocompatibility may be defined as the characteristic of an implant acting in such a way as to allow its therapeutic function to be manifested without secondary adverse affects such as toxicity, foreign body reaction or cellular disruption.

Formable compositions are used to correct surgical defects that may be caused by trauma, pathological disease, surgical intervention or other situations where defects need to be managed in osseous surgery. It is important to have the defect filler in the form of a stable, viscous formable composition to facilitate the placement of the bone growth medium into the surgical site which is usually uneven in shape and depth. In general practice, the surgeon will take the composition on a spatula or other instrument and trowel it into the site or take it in his/her fingers to shape the bone inducing material into the proper configuration to fit the site being corrected. It is also important that the defect filler be biocompatible and have the correct osmolality and pH and not cause any additional trauma at the surgical site.

Many products have been developed in an attempt to treat this surgical need for a biocompatible formable material. One such example is autologous bone particles or segments recovered from the patient. When removed from the patient, the segments or bone particles are wet and viscous from the associated blood. This works very well to heal the defect but requires significant secondary surgery resulting in lengthening the surgery, extending the time the patient is under anesthesia and increasing the cost. In addition, a significant increase in patient morbidity is attendant in this technique as the surgeon must take bone from a non-involved site in the patient to recover sufficient healthy bone, marrow and blood to perform the defect filling surgery. This leads to significant post-operative pain.

Another product group involves the use of inorganic materials to provide a matrix for new bone to grow at the surgical site. These inorganic materials include hydroxyapatite obtained from sea coral or derived synthetically, and ceramics. Either form may be mixed with a biocompatible carrier, the patient's blood and/or bone marrow to form a gel or a putty. These inorganic materials are generally osteoconductive but are bioinert and do not absorb or become remodeled into natural bone. A ceramic which is osteopromotive and used for growing bone is marketed under the trademark BIO-GLASS®. However, all of the aforementioned consequently remain in place for several months to as long as a few years as a brittle, foreign body in the patient's tissue.

Allograft bone is a logical substitute for autologous bone. It is readily available and precludes the surgical complications and patient morbidity associated with autologous bone as noted above. Allograft bone is essentially a collagen fiber reinforced hydroxyapatite matrix containing active bone morphogenic proteins (BMP) and can be provided in a sterile form. The demineralized form of allograft bone is naturally both osteoinductive and osteoconductive. The demineralized allograft bone tissue is fully incorporated in the patient's tissue by a well established biological mechanism. It has been used for many years in bone surgery to fill the osseous defects previously discussed.

It is well known in the art that for several decades surgeons have used a patient's own blood as a vehicle in which to mix the patient's bone chips or bone powder, or demineralized bone powder so as to form a defect filling paste. Blood is a useful carrier because it is available from the bleeding operative site, is non-immunogenic to the patient and contains bone morphogenic proteins which facilitate wound healing through new bone growth. However, stored blood from other patients has the deficiencies that any blood transfusion would have; such as blood type compatibility, possibility of transmission of disease and unknown concentration of BMP which are to a great extent dependent upon the age of the donor.

While blood contains from forty percent (40%) to fifty percent (50%) cell mass, it is a satisfactory carrier for demineralized bone powder because it contains both mono- and polysaccharides which contribute to the blood viscosity and provide the bulk viscosity to the paste created by mixing the bone powder and blood. Specific monosaccharides in blood are glucose at a concentration of 60-100 mg/100 ml (0.1%) and polysaccharides such as hexose and glucosamine at approximately 0.1%. Glucuronic acid is also present at approximately 0.4-1.4 mg/100 ml (average 0.01%).

The problems inherent with using the patients blood as a carrier for demineralized bone powder are the difficulties of mixing the same at the operating site, the difficulty in obtaining a bone paste consistency which can be easily applied to the surgical area, the guesswork in mixing a usable composition at the site and the problem of having a bone paste or gel which will promote optimum bone replacement growth and not be carried away by the body fluids at the operation site or simply fall out of the bone defect site. In an attempt to solve these and other problems, there have been a number of other attempts using other alternative mixtures and compositions.

Demineralized allograft bone is usually available in a lyophilized or freeze dried and sterile form to provide for extended shelf life. The bone in this form is usually very coarse and dry and is difficult to manipulate by the surgeon. One solution to use such freeze dried bone has been provided in the form of a gel, GRAFTON®, a registered trademark of Osteotech Inc., which is a simple mixture of glycerol and lyophilized, demineralized bone powder of a particle size in the range of 0.1 cm to 1.2 cm (1000 microns to 12,000 microns) as is disclosed in U.S. Pat. No. 5,073,373.

GRAFTON works well to allow the surgeon to place the allograft bone material at the site. However, the carrier, glycerol has a very low molecular weight (92 Daltons) and is very soluble in water, the primary component of the blood which flows at the surgical site. Glycerol also experiences a marked reduction in viscosity when its temperature rises from room temperature (typically 22° C. in an operating room) to the temperature of the patient's tissue, typically 37° C. This combination of high water solubility and reduced viscosity causes the allograft bone material with a glycerol carrier to be "runny" and to flow away from the site almost immediately after placement; this prevents the proper retention of the bone material within the site as carefully placed by the surgeon.

These problems with GRAFTON gel have been attempted to be resolved by using a much larger particle size of allograft bone, specifically lamellae or slivers of bone created by milling or slicing the bone before mixing it with the glycerol carrier. This improves both the bulk viscosity and the handling characteristics of the mixture but still leaves the problem of the fast rate of dissipation of the carrier and some bone due to the solubility of the glycerol carrier. The larger particles of demineralized bone may also retard the development of new bone by the patient because the large bony lamellae do not pack as well as the smaller grainy particles of bone. This will leave more open space and could lengthen the time required to grow new bone and properly fill the defect. Another deficiency of using the bony lamellae is that the ends of the bony fragments are uneven and when packed into the surgical defect, uneven filaments of bone are left protruding out from the defect which can compromise the healing rate.

U.S. Pat. No. 5,290,558, issued 1 Mar. 1994, discloses a flowable demineralized bone powder composition using an osteogenic bone powder with large particle size ranging from about 0.1 to about 1.2 cm. mixed with a low molecular weight polyhydroxy compound possessing from 2 to about 18 carbons including a number of classes of different compounds such as monosaccharides, disaccharides, water dispersible oligosaccharides and polysaccharides.

The advantages of using the smaller bone particle sizes as disclosed in the U.S. Pat. No. 5,073,373 gel patent, issued 17 Dec. 1991, were compromised by using bone lamellae in the shape of threads or filaments and retaining the low molecular weight glycerol carrier. This later prior art is disclosed in U.S. Pat. No. 5,314,476, issued 24 May 1994, and U.S. Pat. No. 5,507,813, issued 16 Apr. 1996, and the tissue forms described in these patents are known commercially as the GRAFTON® Putty and Flex, respectively.

The use of the very low molecular weight glycerol carrier also requires a very high concentration of glycerol to be used to achieve the bulk viscosity. Glycerol and other similar low molecular weight organic solvents are toxic and irritating to the surrounding tissues.

U.S. Pat. No. 5,356,629, issued 18 Oct. 1994, discloses making a rigid composition in the nature of a bone cement to fill defects in bone by mixing biocompatible particles preferably polymethylmethacrylate coated with polyhydroxyethylmethacrylate in a matrix selected from a group which lists hyaluronic acid to obtain a molded semi-solid mass which can be suitably worked for implantation into bone. The hyaluronic acid can also be utilized in monomeric form or in polymeric form preferably having a molecular weight not greater than about one million Daltons. It is noted that the nonbioabsorbable material which can be used to form the biocompatible particles can be derived from xenograft bone, homologous bone, autogenous bone as well as other materials. The bioactive substance can also be an osteogenic agent such as demineralized bone powder, in addition to morselized cancellous bone, aspirated bone marrow and other autogenous bone sources. The average size of the particles employed is preferably about 0.1 to about 3.0 mm, more preferably about 0.2 to about 1.5 mm, and most preferably about 0.3 to about 1.0 mm. It is inferentially mentioned but not taught that particles having average sizes of about 7,000 to 8,000 microns, or even as small as about 100 to 700 microns can be used. This reference, however, is simply a cement used for implantation of hip prosthesis and is not used to promote bone growth.

U.S. Pat. No. 5,830,493, issued 3 Nov. 1998, is directed toward a composite porous body (hyaluronic acid listed in a group of compounds) comprising a porous frame and a surface layer comprising a bioabsorbable polymer material formed on the surface. A bone morphogenetic protein (BMP) is carried on the surface and inside of the composite porous body. There is no demineralization of bone and the reference appears only to be relevant to show the addition of BMP to a bone forming graft.

Another attempt to solve the bone composition problem is shown in U.S. Pat. No. 4,172,128, issued 23 Oct. 1979, which discloses demineralized bone material mixed with a carrier to reconstruct tooth or bone material by adding a mucopolysaccharide to a mineralized bone colloidal material. The composition is formed from a demineralized coarsely ground bone material, which may be derived from human bones and teeth, dissolved in a solvent forming a colloidal solution to which is added a physiologically inert polyhydroxy compound such as mucopolysaccharide or polyuronic acid in an amount which causes orientation when hydrogen ions or polyvalent metal ions are added to form a gel. The gel will be flowable at elevated temperatures above 35° C. and will solidify when brought down to body temperature. Example 25 of the patent notes that mucopolysaccharides produce pronounced ionotropic effects and that hyaluronic acid is particularly responsible for spatial cross-linking. Unfortunately this bone gel is difficult to manufacture and requires a premolded gel form.

U.S. Pat. No. 7,019,192, issued 28 Mar. 2006, discloses a composition for filling bone defects consisting of demineralized bone material (DBM) in a sodium hyaluronate (HY) or carboxymethylcellulose (CMC) excipient formulation. A DBM concentration of up to 50% (w/w) is disclosed but the reference notes that higher concentrations may be impracticably "gritty or sandy." Practical limitations of the '192 patent appear to limit DBM concentrations to no more than 35% (w/w).

Another prior art product is the formulation of demineralized allograft bone particles in collagen. Both bovine and human collagen have been used for this application. Bovine collagen carries the risk of an immunogenic reaction by the recipient patient. Recently, it has been found that a disease of cattle, bovine spongioform encephalopathy (BSE) is transmitted from bovine tissue to humans. Thus, bovine tissue carries a risk of disease transmission and is not a desirable carrier for allograft tissue.

Human collagen is free of these animal based diseases. However, collagen absorbs slowly in the human body, particularly in a bony site with usually a low degree of vascularity. The slow absorption of collagen can delay the growth of new bone and result in the formation of scar tissue at the site. This could result in a non-bony healing and a result with much less tensile strength.

Accordingly, the prior art as embodied in the glycerol and other carrier based technology to deliver demineralized allograft bone to a surgical osseous site is replete with problems and only partially addresses the problems inherent in the correcting surgical defects.

SUMMARY OF THE INVENTION

The subject formulation is a complex mixture of bone particles and a novel combination of viscous high molecular weight materials showing significantly higher osteoinductive activity compared to previously known materials. A combination of carboxymethylcellulose and sodium hyaluronate have been determined to permit increased concentrations of bone material. Whereas previous formulations were limited in the amount of bone mass able to be incorporated, generally no more than about 35%, this novel formulation supports incorporation of significantly greater amounts of bone, with increased osteoinductivity resulting therein. A sodium based phosphate buffer is used as a carrier or delivery vehicle for the osteoinductive particles which are mixed with living cells and/or cell elements or with a bone growth additive. The viscous formulation is designed to present the bone material and its bone morphogenetic proteins (BMP), and the macro-structure of the bone particles, serving both as an osteoconductive matrix and to signal the patient's tissue and cells to initiate the growth of new bone (osteoinduction). The formulation is used primarily in contact with bleeding bone. This condition is created either from trauma or a surgical procedure that may involve drilling, sawing, grinding or scraping the bone to achieve a bleeding condition. In surgery, the bone is traumatized or surgically cut exposing blood capillaries, Haversian canals (micro-channels in the bone), periosteum (the protective tissue lining around bone), muscle and other structures in the surgical site. Bleeding at the site is considered a favorable condition to enhance healing of the wound site by bringing to the site the patient's own cytokines, i.e., proteins and other molecules which are the body's mechanism to carry out the healing process. Any interference with the blood cell mechanism would be considered non-biocompatible and an adverse outcome.

In order for the bone material to be osteoinductive, interference either from the traumatized cells or the formulation must be at a minimum, i.e., a biocompatible condition should be established and maintained. Several specific properties have been established in the formulation to create a functional and therapeutic material. These properties pertain to both physical characteristics and to the achieving of a biocompatible or physiologically friendly condition.

It is an object of the invention to utilize bone material in a particle size that is useful to achieve the necessary malleability characteristics while allowing maximization of the amount of bone in the formulation.

It is an additional object of the invention to use a non toxic aqueous solution carrier with a sodium phosphate buffer for the bone particles to present the composition in a state of physiological osmolality at the wound site.

It is also an object of the invention to create a bone defect material which can be easily handled by the physician and does not degenerate when contacting blood flow at the surgical site.

It is another object of the invention to create a bone defect material which uses cellular material such as living cells and cell elements, growth factors and anti-infective agents.

It is still another object of the invention to create a bone defect material which has a stable viscosity at a temperature range from 22° to 37° C. It is an additional object of the invention to create a bone defect material with a physiological osmotic pressure and pH.

It is yet another object of the invention to use a growth factor in the bone composition.

It is another object of the invention to create a bone defect material with approximately 38%-42% (w/w) DBM exhibiting increased osteoinductive activity and sufficient malleability.

DESCRIPTION OF THE INVENTION

The present invention is directed towards a demineralized or partially demineralized bone particle composition used to heal bone defects.

A formable surgical composition with a useful bulk viscosity has been achieved by using a combination of soluble biomaterials. The balance of the carrier formulation is an aqueous solution and preferably includes the addition of a material component, namely, a sodium based phosphate buffer in a sterile saline or salt carrying water which avoids the toxic problems with the high concentrations of the low molecular weight organic solvents of the prior art.

The particle size of demineralized, lyophilized, allograft bone when mixed with a combination of high molecular weight stable viscosity biomaterials in a suitable carrier produces a formable composition with increased bone inducing properties. The formable property permits the surgeon to shape the bone composition to exactly fit the surgical defect. Manipulation of the "lump" of formable bone composition may be done without it sticking to the gloves of the surgeon, behaving somewhat like a wet clay used in sculpting.

It is an important aspect of the present invention that the implant matrix must remain at the wound site and not be washed away by the flowing blood and other fluids brought to the site by the healing mechanism. This is achieved by the viscous state of the carrier. While viscous, the aqueous carrier is a high molecular weight macromolecule held together with water linkages (hydrogen bonds) and is not readily dissolved and washed away by the blood and fluids at the wound site.

Thus, the therapeutic formable bone composition will not be dissipated by being washed away and is present for increased osteoinductive activity.

The amount of demineralized bone material (DBM) is maximized in the present application to achieve the optimum balance of osteoinductivity and physical handling properties. Too much matrix bone creates a gritty or sandy condition in which the DBM is not enclosed by the surrounding viscous matrix causing the DBM bone particles to be easily washed away and is not flowable or easily formed into an implant for the defect area by the surgeon. Conversely, if the bone concentration is too low, the osteoinductivity would be less than optimum. A maximum bone concentration in the composition is obtained in the range of about 38% to about 42%, with a preferred concentration of about 40% (w/w).

The types of demineralized bone used in the invention are cortical, corticocancellous and cancellous bone particles. While the preferred embodiment uses allograft bone, xenograft bone which has been treated could also be used. Similarly living cells and cell elements and/or growth factors can be added to the composition.

The inventive formulation uses a unique carrier formed of a combination of carboxymethylcellulose (CMC) having a 200,000 to 500,000 Daltons molecular weight and sodium hyaluronate (HY) and its derivatives having a 700,000 Daltons molecular weight in a ratio of about 20:1 (CMC to HY). This combination is used at an approximately 11% concentration in sterile water or phosphate buffered saline to achieve the bulk viscosity required for the formulation. It should be understood that 100% CMC is not osteoinductive and will be dissolved in the first 1-7 days after implantation. The osteoactive cycle must occur in 10 days. Otherwise, scar tissue rather then bone will form. The combined HY and CMC allows the bone concentration of the putty composition to have good flowable properties allowing the same to be easily formed and placed in the defect area while keeping the bone particles in the defect site during the osteoactive cycle and thus promote significant increased bone growth above that presently found in other bone putties.

The carrier for the formable bone have a good bulk viscosity with: 1) carboxymethylcellulose (CMC) at 200,000 to 500,000 Daltons molecular weight, and 2) sodium hyaluronate (HY) at 700,000 Daltons molecular weight.

It is important to note that the body has many complex and redundant mechanisms to maintain its biochemical balance. The blood pH can be adjusted by several means to its normal, physiologic pH. Hence the presence of a non-physiologic material at the site of a bleeding bone wound will eventually be overcome and any non-biocompatible condition will return to normal pH. The preferred formulation will start out and maintain pH within the range of 6.5 to 7.5 without stressing the body's biochemical mechanisms when the bone composition material is applied at the wound site.

In achieving physiologic pH, the formulation uses a phosphate buffer based on an aqueous system of the two phosphate anions, $HPO_4^{-2}$ and $H_2PO_4^{-1}$. This buffer system is used both to neutralize the acid used to demineralize the bone and to buffer the combined CMC/HY carrier. It is important to neutralize the acid (hydrochloric acid) used to demineralize the bone so as to assure that there is no residue of this very strong acid which could overwhelm the buffering capacity of the phosphate system used to buffer the combination of excipients in the carrier.

The pH is adjusted to the physiologic a range of 6.5 to 7.5 pH or preferably 7.2-7.4 pH by using either or both of dibasic sodium phosphate or monobasic sodium phosphate and adjusting the solution with saline, i.e., a sodium chloride solution. The sodium chloride is chosen instead of only water so as to control the final osmolality of the formulation to preclude dehydration of the surrounding cells.

The buffer introduced contains sodium and phosphate ions which will remain in solution due to the high solubility of sodium phosphate. Calcium ions in the extracellular fluid will react with the phosphate ions to result in the precipitation of insoluble calcium phosphate salt. More phosphate ions will ionize from the associated state of the phosphate buffer to introduce more phosphate ions that will, in turn react with more calcium and precipitate yet more insoluble calcium phosphate. The calcium phosphate will deposit at the wound site where the buffered formulation was placed by the surgeon. This results in an increase in the presence of calcium at the wound site in the precise location where calcium will be needed to grow new bone.

Thus, the invention induces the presence of soluble calcium at the bone defect site which will encourage new bone growth through the normal biological mechanism. The phosphate buffer attracts calcium cations to the site from the surrounding healthy bone and creates an equilibrium concentration of the calcium precisely at the site of healing where it is most desirable to grow new bone.

It is a well known principal of physiology that osmotic pressure must be maintained within a narrow range to assure healthy conditions for the many cell types present in normal or surgically wounded cells. The condition of normal osmotic pressure is referred to as an isotonic state and is quantified in humans by the value of about 300 mOsmol/Kg. The carboxymethylcellulose and sodium hyaluronate formulation is buffered to isotonic conditions using sodium chloride as the ionic salt to supplement the sodium phosphate. Were this combination to be buffered without the supplemental saline, the final excipient formulation would only reach an osmolality of less than 50 mOsmol/Kg.

At this low osmolality, the extra cellular environment at the wound site would be in a state of hypotonicity and result in the inflow of large quantities of water to the cells and blood cells at the wound site to normalize the osmotic pressure. This will result in a greater than optimum degree of hydration of the cells and inhibit wound healing in general and bone growth in particular. Hemolysis may occur due to excess fluid in the cells.

It is envisioned that suitable amounts of bone morphogenic proteins (BMP) can be added to the putty composition at any stage in the mixing process to induce accelerated healing at the bone site. BMP directs the differentiation of pluripotential mesenchymal cells into osteoprogenitor cells which form osteoblasts. The ability of freeze dried demineralized cortical bone to transfer this bone induction principle using BMP present in the bone is well known in the art. However, the amount of BMP varies in the bone depending on the age of the bone donor and the bone processing. Sterilization is an additional problem in processing human bone for medical use as boiling, autoclaving and irradiation over 2.0 Mrads is sufficient to destroy or alter the BMP present in the bone matrix.

A product with satisfactory formability and handling properties, and increased osteoinductive characteristics, would have a carboxymethylcellulose (CMC) molecular weight of approximately 200,000 to 500,000 Daltons and concentration of 5%-7%; a sodium hyaluronate (HA) molecular weight of 700,000 Daltons and concentration of 0.1%-0.7%, most preferably 0.3%; and a bone concentration of 38% to 42% with a particle size of 100-820 microns in a phosphate buffered solution (PBS) carrier.

Additives which are beneficial to bone growth and are added into the formable composition are living cells and cell elements such as chondrocytes, red blood cells, white blood cells, platelets, blood plasma, bone marrow cells, mesenchymal stem cells, pluripotential cells, osteoblasts, osteoclasts, and fibroblasts, epithelial cells, and endothelial cells. These cells or cell elements or combinations of the same are present at a concentration of $10^5$ to $10^8$ per cc of carrier and are added into the composition at time of surgery.

Growth factor additives which can be used in the present invention either at the time of packaging or at surgery depending on the stability of the growth factor are transforming growth factor (TGF-beta), insulin growth factor (IGF-1); platelet derived growth factor (PDGF), vascular endothelial growth factor (VEGF), fibroblast growth factor (FGF) native and variants of the same (numbers 1-23), bone morphogenic proteins (BMP)(numbers 2, 4, 7), osteopontin, growth hormones such as somatotropin, cellular attractants and attachment agents.

Additional additives which can be included are antiviral additives such as those effective against HIV and hepatitis; antimicrobial and/or antibiotics such as erythromycin, bacitracin, triclosan, neomycin, penicillin, polymyxin B, tetracycline, viomycin, chloromycetin, streptomycin, cefazolin, ampicillin, azactam, tobramycin, clindamycin and gentamycin.

It is also envisioned that amino acids, peptides, vitamins, co-factors for protein synthesis; hormones; endocrine tissue or tissue fragments; synthesizers; enzymes such as collagenase, peptidases, oxidases; polymer cell scaffolds with parenchymal cells; angiogenic drugs and polymeric carriers containing such drugs; collagen lattices; biocompatible surface active agents, antigenic agents; cytoskeletal agents; cartilage fragments can all be used additives, In the following example the components of the composition used is as follows:

EXAMPLE

A malleable putty of 6.1% (w/w) carboxymethylcellulose (CMC) and 0.3% sodium hyaluronate (HY) (w/w) in a phosphate buffered solution with allograft bone demineralized powder having a size ranging from 100 to 850 microns at 40% (w/w).

Freeze dried demineralized allograft bone powder (DBM) and CMC were mixed with HY in a phosphate buffered solution containing dibasic sodium phosphate, monobasic sodium phosphate, sodium chloride solution, and USP purified water at final concentrations (w/w) of: 40% DBM, 6.1% CMC, 0.3% HA, 2.725% dibasic sodium phosphate, 0.283% monobasic sodium phosphate, 0.572% sodium chloride, and 50.023% water. The mixture was well stirred to provide a malleable putty with excellent formability and increased osteoinductive characteristics.

Living cells and cell elements such as chondrocytes, red blood cells, white blood cells, platelets, blood plasma, bone marrow cells, mesenchymal stem cells, pluripotential cells, osteoblasts, osteoclasts, and fibroblasts, epithelial cells, and endothelial cells have been added into the composition. These cells or cell elements or combinations of the same are present at a concentration of $10^5$ to $10^8$ per cc of carrier and are added into the composition at time of surgery.

Similarly growth factor additives which can be used in the present composition either at the time of packaging or at surgery depending on the stability of the growth factor are transforming growth factor (TGF-beta), insulin growth factor (IGF-1); platelet derived growth factor (PDGF), vascular endothelial growth factor (VEGF), fibroblast growth factor (FGF) (numbers 1-23) and variants of same, bone morphogenic proteins (BMP)(numbers 2, 4, 7), osteopontin, growth hormones such as somatotropin cellular attractants and attachment agents. Fibroblast growth factor is added in the amount of 2 to 4 milligrams in 10 cc of carrier solution.

The mixing of the demineralized bone powder into the excipient solution is undertaken in a sterile chamber. The mixed formable bone composition is then placed in a sterile container such as an impervious syringe barrel or vial, sealed and placed in a sterile sealed package to which stable growth factors are added with the cell material and unstable growth factors added to the composition at the time of surgery.

One process commonly used to achieve sterility is to irradiate the excipient materials and then continue with aseptic mixing of the bone. Irradiation sources of either electron beam or gamma (Cobalt 60 isotope) are commercially available.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What we claim is:

1. A composition for application to a bone defect site, the composition consisting of demineralized or partially demineralized osteoinductive bone particles, a carrier, and optionally, one or more of (i) one or more growth factor additives, (ii) a cellular material taken from the group consisting of living cells and cell elements, (iii) one or more antiviral additives effective against HIV and hepatitis, and (iv) an antimicrobial and/or antibiotic selected from the group consisting of one or more of erythromycin, bacitracin, triclosan, neomycin, penicillin, polymyxin B, tetracycline, viomycin, chloromycetin, streptomycin, cefazolin, ampicillin, azactam, tobramycin, clindamycin, and gentamycin;

wherein the bone particles range from about 100 to 850 microns in size, and are present in an amount ranging from about 38% to about 42% (w/w) of the composition; and wherein the carrier consists of carboxymethylcellulose and sodium hyaluronate in one or more of a phosphate buffered aqueous solution, saline, or sterile water, wherein the carboxymethylcellulose and sodium hyaluronate are present in a weight ratio of about 20:1, and wherein the carboxymethylcellulose has a molecular weight in a range of from about 200,000 to about 500,000 Daltons.

2. The composition of claim 1, wherein the bone particles are present in an amount of about 40% (w/w) of the composition.

3. The composition of claim 1, wherein the bone particles are from allograft bone.

4. The composition of claim 3, wherein said allograft bone is selected from cortical bone, corticocancellous bone, cancellous bone, or combinations thereof.

5. The composition of claim 1, wherein the bone particles are from xenograft bone.

6. The composition of claim 4, wherein said xenograft bone is selected from cortical bone, corticocancellous bone, cancellous bone, or combinations thereof.

7. The composition of claim 1, wherein the carboxymethylcellulose is present in an amount ranging from about 5% to about 11% (w/w) of the carrier.

8. The composition of claim 1, wherein the sodium hyaluronate has a molecular weight of at least 700,000 Daltons.

9. The composition of claim 1, wherein the sodium hyaluronate is present in an amount ranging from about 0.1% to about 0.7% (w/w) of the carrier.

10. The composition of claim 1, wherein the sodium hyaluronate is present in an amount of about 0.3% (w/w) of the carrier.

11. The composition of claim 1, wherein said one or more growth factor additives is selected from a transforming growth factor, an insulin growth factor, a platelet derived growth factor, a vascular endothelial growth factor, a fibroblast growth factor, a bone morphogenic protein, osteopontin, cellular attractants and attachment agents, or a growth hormone.

12. The composition of claim 11, wherein said fibroblast growth factor is present in the amount of 2 to 4 milligrams in 10 cc of carrier solution.

13. The composition of claim 1, wherein said cellular material is selected from chondrocytes, red blood cells, white blood cells, platelets, bone marrow cells, mesenchymal stem cells, pluripotential cells, osteoblasts, osteoclasts, fibroblasts, epithelial cells, or endothelial cells.

14. The composition of claim 13, wherein said cellular material is present at a concentration of $10^5$ to $10^8$ cells per cc of the carrier.

15. The composition of claim 1, wherein the pH of said composition ranges from 6.5 to 7.5.

16. The composition of claim 11, wherein said growth hormone is somatotropin.

* * * * *